United States Patent [19]
Iwamoto et al.

[11] Patent Number: 5,639,893
[45] Date of Patent: Jun. 17, 1997

[54] PROCESS FOR PRODUCING OCTAHYDROCOUMARINS AND SAME AS A PRODUCT OF SUCH PROCESS

[75] Inventors: Koji Iwamoto; Shin Tanaka, both of Ehime, Japan

[73] Assignee: Sumitomo Chemical Company, Limited, Osaka, Japan

[21] Appl. No.: 680,063

[22] Filed: Jul. 17, 1996

[30] Foreign Application Priority Data

Jul. 13, 1995 [JP] Japan .................................. 7-177334

[51] Int. Cl.$^6$ .................................................. C07D 311/06
[52] U.S. Cl. ........................................................ 549/290
[58] Field of Search ............................................. 549/290

[56] References Cited

U.S. PATENT DOCUMENTS

| | | | |
|---|---|---|---|
| 3,859,311 | 1/1975 | Symon et al. | 260/343.2 R |
| 3,891,678 | 6/1975 | Verheijen et al. | 260/343.2 R |
| 3,936,473 | 2/1976 | Symon et al. | 260/343.2 R |
| 3,998,851 | 12/1976 | Reichenbacher et al. | 260/343.2 R |
| 5,218,129 | 6/1993 | Shirafuji et al. | 549/290 |

FOREIGN PATENT DOCUMENTS

| | | |
|---|---|---|
| 420 532 | 4/1991 | European Pat. Off. . |
| 526 231 | 2/1993 | European Pat. Off. . |
| 533 378 | 3/1993 | European Pat. Off. . |

OTHER PUBLICATIONS

CA 98:197945 Synthesis and . . . benzopyran—2–one. Sanghvi et al., 1983.
CA 99:194466 Synthesis of . . . mevalonic acid. Carganico et al., 1983.
The Journal of the American Chemical Society, vol. 62 p. 3067 (1940).
The Journal of the American Chemical Society, Vo. 62, p. 283 (1940).
Journal of the Chemical Society, Perkin Transaction, II p. 431 (1988).
Journal of the Pharmaceutical Society of Japan, 74, p. 895 (1956).
Patent Abstracts of Japan, vol. 10, No. 28 (C–236) [2085], Feb. 4, 1986 and JP–A–60 181082 (Sumitomo Kagaku Kogyo K.K. Sep. 14, 1985.
De Benneville et al., "The Hydrogenation of Coumarin and Related Compounds," Journal of the American Chemical Society, vol. 62, 1940, Columbus, Ohio, pp. 283–287.

*Primary Examiner*—Joseph McKane
*Attorney, Agent, or Firm*—Cushman Darby & Cushman IP Group of Pillsbury Madison & Sutro, LLP

[57] ABSTRACT

The present invention involves the production of octahydrocoumarins from coumarins and/or 3,4-dihydrocoumarins in good yields by a simple process which can be industrially carried out, by reducing coumarins and/or 3,4-dihydrocoumarins to octohydrocoumarins with hydrogen in the presence of an alcohol and a ruthenium catalyst, and optionally heating resultant 3-(2-hydroxycyclohexyl) propionate contained in the reduction reaction mixture to conduct cyclization/dealcoholization and convert same to octohydrocoumarins.

15 Claims, No Drawings

PROCESS FOR PRODUCING OCTAHYDROCOUMARINS AND SAME AS A PRODUCT OF SUCH PROCESS

BACKGROUND OF THE INVENTION

1. Field of the Invention

The present invention relates to a process for producing octahydrocoumarins by reducing coumarins and/or dihydrocoumarins with hydrogen in the presence of an alcohol and a ruthenium catalyst, and optionally further heating the reaction mixture obtained by the reduction reaction. The present invention further relates to octahydrocoumarins produced as a result of that process. The octahydrocoumarins are important compounds in the perfume industry and are also useful as synthesis intermediates in the chemical industry.

2. Description of Related Art

As conventional processes for reducing coumarins and/or dihydrocoumarins to produce octahydrocoumarins, which are important compounds in the perfume and chemical industry, there has hitherto been known a process of reducing coumarin with hydrogen in a glacial acetic acid in the presence of a platinum oxide catalyst, e.g., Pharmaceutical Journal, 74, 895–898(1954), the disclosure of which is incorporated herein by reference, and a process of reducing coumarin with hydrogen in cycloheptane or ethanol in the presence of a Raney nickel or copper-chromite catalyst, e.g., J. Am. Chem. Soc., 62, 283–287(1940), the disclosure of which is also incorporated herein by reference.

However, the conventional processes mentioned above are not industrially satisfactory. Regarding the process of reducing coumarin with hydrogen in the presence of a platinum oxide catalyst, a large amount of expensive platinum oxide is used and the yield of octahydrocoumarin is not satisfactory. Regarding the process of reducing coumarin in the presence of a Raney nickel or copper-chromite catalyst, the reduction of coumarin is carried out under a hydrogen pressure between 100 and 200 atm and the yield of octahydrocoumarin is not satisfactory.

SUMMARY OF THE INVENTION

An object of the present invention is therefore to provide a process for producing octahydrocoumarins from coumarins and/or 3,4-dihydrocoumarins which is industrially satisfactory.

A further object of the present invention is to provide a process for producing octahydrocoumarins from coumarins and/or 3,4-dihydrocoumarins which results in satisfactory yields of the octahydrocoumarins.

Another object of the present invention is to provide octahydrocoumarins in a satisfactory yield as a product of an industrially satisfactory process for reducing coumarins and/or 3,4-dihydrocoumarins.

The above objects and others are accomplished by the process of the present invention, wherein octahydrocoumarins can be obtained in good yields by reducing coumarins and/or dihydrocoumarins with hydrogen in the presence of an alcohol and a ruthenium catalyst, and optionally further heating the reaction mixture obtained by the reduction reaction.

DETAILED DESCRIPTION OF THE INVENTION

The present invention provides a process for producing octahydrocoumarins represented by the general formula (1):

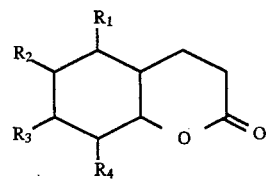

(1)

wherein $R_1$ to $R_4$ respectively indicate a hydrogen atom or an alkyl group having 1 to 5 carbon atoms, which process comprises the step of reducing coumarins represented by the general formula (2):

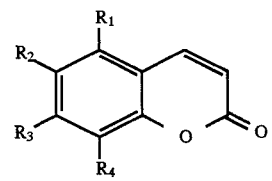

(2)

wherein $R_1$ to $R_4$ respectively indicate a hydrogen atom or an alkyl group having 1 to 5 carbon atoms, and/or reducing 3,4 dihydrocoumarins represented by the general formula (3):

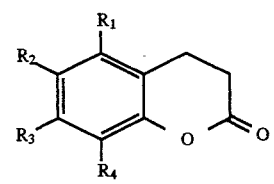

(3)

wherein $R_1$ to $R_4$ respectively indicate a hydrogen atom or an alkyl group having 1 to 5 carbon atoms, with hydrogen in the presence of an alcohol and a ruthenium catalyst.

Suitable examples of the coumarins, represented by the general formula (2) and used in the process of the present invention include, without limitation, coumarin, 5-methylcoumarin, 6-methylcoumarin, 7-methylcoumarin, 8-methylcoumarin, 5-ethylcoumarin, 6-ethylcoumarin, 7-ethylcoumarin, 8-ethylcoumarin, 5,6-dimethylcoumarin, 5,7-dimethylcoumarin, 5,8-dimethylcoumarin, 6,7-dimethylcoumarin, 6,8-dimethylcoumarin, 7,8-dimethylcoumarin, 5-methyl-6-ethyl-coumarin, 5-methyl-7-ethyl-coumarin, 5-methyl-8-ethyl-coumarin, 6-methyl-7-ethyl-coumarin, 6-methyl-8-ethyl-coumarin, 7-methyl-8-ethyl-coumarin, 5-ethyl-6-methyl-coumarin, 5-ethyl-7-methyl-coumarin, 5-ethyl-8-methyl-coumarin, 6-ethyl-7-methyl-coumarin, 6-ethyl-8-methyl-coumarin, 7-ethyl-8-methyl-coumarin, among others.

The coumarins may be used alone or in a mixture of two or more.

Suitable examples of the 3,4-dihydrocoumarins, represented by the general formula (3) and used in the process of the present invention include, without limitation, 3,4-dihydrocoumarin, 5-methyl-3,4-dihydrocoumarin, 6-methyl-3,4-dihydrocoumarin, 7-methyl-3,4-dihydrocoumarin, 8-methyl-3,4-dihydrocoumarin, 5-ethyl-3,4-dihydrocoumarin, 6-ethyl-3,4-dihydrocoumarin, 7-ethyl-3,4-dihydrocoumarin, 8-ethyl-3,4-dihydrocoumarin, 5,6-dimethyl-3,4-dihydrocoumarin, 5,7-dimethyl-3,4-dihydrocoumarin, 5,8-dimethyl-3,4-dihydrocoumarin, 6,7-dimethyl-3,4-dihydrocoumarin, 6,8-dimethyl-3,4-dihydrocoumarin, 7,8-dimethyl-3,4-dihydrocoumarin, 5-methyl-6-ethyl-3,4-dihydrocoumarin, 5-methyl-7-ethyl-3,4-dihydrocoumarin, 5-methyl-8-ethyl-3,4-dihydrocoumarin, 6-methyl-7-ethyl-3,4-dihydrocoumarin, 6-methyl-8-ethyl-3,4-dihydrocoumarin, 7-methyl-8-ethyl-3,4-dihydrocoumarin, 5-ethyl-6-methyl-3,4-dihydrocoumarin, 5-ethyl-7-methyl-3,4-dihydrocoumarin, 5-ethyl-8-methyl-3,4-dihydrocoumarin, 6-ethyl-7-methyl-3,4-dihydrocoumarin, 6-ethyl-8-methyl-3,4-dihydrocoumarin, 7-ethyl-8-methyl-3,4-dihydrocoumarin, among others.

The 3,4-dihydrocoumarins may be used alone or in a mixture of two or more. Further, one or more coumarins may be used along with one or more 3,4-dihydrocoumarins.

In the present invention, the alcohol is represented by the general formula R-OH, wherein R is an alkyl group, and those where R is an alkyl group which has 1 to 6 carbon atoms are preferred in view of the cost of the alcohol used. Suitable examples thereof include without limitation methanol, ethanol, propanol, isopropanol, amyl alcohol, pentanol, cyclopentanol, hexanol, cyclohexanol, among others. Among the above examples, methanol and ethanol are preferably used.

The above alcohols may be used alone or in a combination of two or more.

An amount of the alcohol used is usually not less than about 0.5 mol, preferably from about 0.5 to about 100 mol, more preferably from about 1 to about 50 mol, and most preferably from about 1 to about 10 mol, based on 1 mol of the coumarins and/or 3,4-dihydrocoumarins as the raw material.

The ruthenium catalyst used for the reduction reaction in the present invention contains ruthenium having a valence of 0 to 6, and suitable examples thereof include, without limitation, metal ruthenium, ruthenium chloride, ruthenium oxide, and organic ruthenium compounds such as ruthenium carbonyl, ruthenocene, among others. Ruthenium having a valence of 0 to 4 is preferred and metal ruthenium is particularly preferred. There can also be used for the ruthenium catalyst those wherein the above examples of rutheniums are supported on a carrier comprising a group 2, 13, 14, or 16 elements of the periodic table or compounds thereof, such as carbon, alumina, silica gel, barium sulfate, among others.

The above ruthenium catalysts may be used alone or in a combination of two or more.

In the case of using a supported ruthenium catalyst, the content of ruthenium atom supported on a carrier is usually from about 0.1 to about 20% by weight, preferably from about 1 to about 10% by weight, more preferably from about 1 to about 5% by weight, based on the total amount of the catalyst.

The amount of ruthenium catalyst varies depending on the amount of ruthenium supported on a carrier when a supported ruthenium catalyst is used. When the amount of ruthenium catalyst is too small, the reaction rate is low. On the other hand, when the amount is too large, the high cost of the catalyst becomes impractical.

Therefore, the amount of ruthenium atom contained in the ruthenium catalyst, whether supported on a carrier or not, is practically from about 0.0001 to about 1% by weight, preferably from about 0.001 to about 0.5% by weight and more preferably from about 0.001 to about 0.3% by weight, based on the total amount of the coumarins and/or 3,4-dihydrocoumarins present in the reaction mixture. It is also possible to reuse the ruthenium catalyst used for the reduction reaction.

In view of the reaction rate and the inhibition of a decomposition reaction of the raw material, the reaction temperature of the reduction reaction is preferably maintained from about 50° C. to about 250° C., more preferably from about 100° C. to about 200° C. A hydrogen partial pressure varies depending on the kind of the ruthenium catalyst, but is generally from about 0.5 to about 100 atm, preferably from about 1 to about 80 atm, and more preferably from about 5 to about 50 atm. Inert gases, such as nitrogen, helium, argon, carbon dioxide, and the like, may coexist in the vapor phase with hydrogen.

As a reaction product of the reduction reaction in the presence of the alcohol in the present invention, 3-(2-hydroxycyclohexyl) propionates represented by the general formula (4):

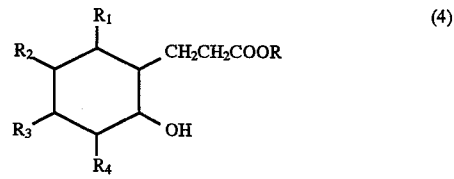

wherein $R_1$ to $R_4$ respectively indicate a hydrogen atom or an alkyl group having 1 to 5 carbon atoms, and R is an alkyl group of an alcohol used in the reduction reaction, are occasionally produced.

Accordingly, 3-(2-hydroxycyclohexyl) propionates are occasionally contained in the reaction mixture obtained by the reduction reaction.

Conversion of the 3-(2-hydroxycyclohexyl) propionates to octahydrocoumarins can be easily obtained by the intramolecular dealcoholization reaction of the 3-(2-hydroxycyclohexyl) propionates by heating under normal pressure or reduced pressure. Accordingly, 3-(2-hydroxycyclohexyl) propionates formed in the process of the reduction reaction can be easily converted into the objective octahydrocoumarins by heating the reduction reaction mixture.

On the other hand, when no alcohol is present in the reaction mixture, cyclohexylpropionic acids represented by the general formula (5):

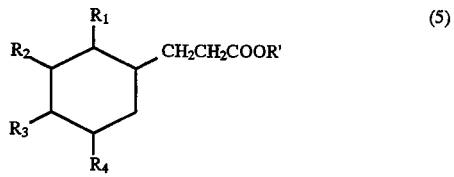

wherein $R_1$ to $R_4$ respectively indicate a hydrogen atom or an alkyl group having 1 to 5 carbon atoms, and R' is hydrogen atom or other than an alkyl group of an alcohol used in the reduction reaction, are produced. The resultant cyclohexylpropionic acids cannot be easily converted into octahydrocoumarins, and, therefore, the yield and selectivity of the octahydrocoumarins are lowered.

In view of the reaction rate of the intramolecular dealcoholization reaction and the inhibition of a decomposition reaction of 3-(2-hydroxycyclohexyl) propionates, the heating temperature is preferably maintained from about 50° C. to about 300° C., more preferably from about 100° C. to about 200° C. Regarding the heating process, the reduction reaction mixture obtained may be heated again to the reaction temperature of the intramolecular dealcoholization reaction after cooling the reduction reaction mixture, or the reduction reaction mixture obtained may be continuously maintained at the reaction temperature of the intramolecular dealcoholization reaction.

The intramolecular dealcoholization reaction of 3-(2-hydroxycyclohexyl) propionates may be conducted by heating without using a catalyst, or with using an acid or a base as a catalyst. Suitable examples of the acid include without limitation mineral acids (e.g., hydrochloric acid, sulfuric acid, phosphoric acid, perchloric acid, and the like), carboxylic acids (e.g., palmitic acid, stearic acid, phthalic acid, adipic acid, and the like) and solid acids (e.g., active carbon, zeolite, acidic ion exchange resin, and the like). Suitable examples of the base include without limitation sodium hydroxide, potassium hydroxide, sodium carbonate, amines, basic ion exchange resin, among others.

It is also possible to reuse the catalyst used for the intramolecular dealcoholization reaction.

The amount of the catalyst used in the intramolecular dealcoholization reaction is from about 0.01 to about 10% by weight, based on the amount of 3-(2-hydroxycyclohexyl) propionates.

The intramolecular dealcoholization reaction is usually conducted after removing the ruthenium containing catalyst from the reduction reaction mixture. In the intramolecular dealcoholization reaction, the above-described acid or base catalyst is optionally added to the reduction reaction mixture and the intramolecular dealcoholization reaction of 3-(2-hydroxycyclohexyl) propionates is carried out to obtain octahydrocoumarin, while the alcohol as the solvent or product of the intramolecular dealcoholization reaction is distilled off from the mixture.

Octahydrocoumarins obtained in the process of the present invention may be a mixture of cis- and trans-octahydrocoumarins. The mixture may be used as it is, or an isomer of the resultant octahydrocoumarins may be purified and separated.

According to the present invention, octahydrocoumarins can be efficiently produced from coumarins and/or 3,4-dihydrocoumarins, as an important compound in the perfume and chemical industry, in good yields by a simple process which can be industrially carried out.

The following Examples and Comparative Examples further illustrate the present invention in detail but are not to be construed to limit the scope thereof. It is further understood that the inventors contemplate variations on the parameters and components of the process for producing octahydrocoumarins described herein, within the scope of the present invention and that described in the related Japanese Patent Application No. 07-177334, filed Jul. 13, 1995, the disclosure of which is hereby incorporated by reference.

EXAMPLES

Example 1

3,4-dihydrocoumarin (100 g), a catalyst (5 g) composed of active carbon and ruthenium supported thereon in an amount of 5% by weight based on the total catalyst, and methanol (100 g) as the solvent were charged in an autoclave made of SUS (internal volume: 1000 ml). After heating to 100° C., the inside of the autoclave was pressurized to 15.5 kg/cm$^2$G with hydrogen and the reduction reaction was conducted for 10 hours.

After the completion of the reduction reaction, the ruthenium catalyst was removed from the reduction reaction mixed solution by filtration to obtain 198 g of the reduction reaction mixture. The resultant reduction reaction mixture was analyzed by gas chromatography. As a result, 63% of 3-(2-hydroxycyclohexyl)methyl propionate and 26% of octahydrocoumarins were contained in the reduction reaction mixture, but 3,4-dihydrocoumarin was not detected.

The solvent was removed from the resultant reduction reaction mixture (67 g) by a simple distillation under a normal pressure. Then, a simple distillation was conducted by heating at a maximum temperature of 150° C. under a pressure of 8 mmHg, thereby conducting the intramolecular dealcoholization reaction. As a result, 28 g of an effluent was obtained. The resultant effluent was analyzed by gas chromatography. As a result, 99% by weight of octahydrocoumarin was contained in the resultant effluent, but 3-(2-hydroxycyclohexyl)methyl propionate was not detected. The isolated yield of octahydrocoumarin which was converted into the yield based on the charged amount of 3,4-dihydrocoumarin was 78%.

Example 2

To 63 g of the reduction reaction mixture obtained by the same method described in Example 1 was added 0.2 g of an aqueous solution containing 20% by weight of NaOH, and the solvent was removed by conducting a simple distillation under a normal pressure. Then, a simple distillation was conducted by heating at a maximum temperature of 150° C. under a pressure of 8 mmhg, thereby conducting the intramolecular dealcoholization reaction. As a result, 28 g of an effluent was obtained. The resultant effluent was analyzed by gas chromatography. As a result, 98% by weight of octahydrocoumarin was contained in the resultant effluent, but 3-(2-hydroxycylohexyl)methyl propionate was not detected. The isolated yield of octahydrocoumarin which was converted into the yield based on the charged amount of 3,4-dihydrocoumarin was 82%.

Example 3

To 67 g of the reduction reaction mixture obtained by the same method described in Example 1 was added 0.02 g of concentrated sulfuric acid, and the solvent was removed by conducting a simple distillation under a normal pressure. Then, a simple distillation was conducted by heating at a maximum temperature of 150° C. under a pressure of 8 mmhg, thereby conducting the intramolecular dealcoholization reaction. As a result, 18 g of an effluent was obtained. The resultant effluent was analyzed by gas chromatography. As a result, 96% by weight of octahydrocoumarin was contained in the resultant effluent, but 3-(2-hydroxycyclohexyl)methyl propionate was not detected. The isolated yield of octahydrocoumarin which was converted into the yield based on the charged amount of 3,4-dihydrocoumarin was 50%.

Example 4

3,4-dihydrocoumarin (100 g), a catalyst (5 g) composed of active carbon and ruthenium supported thereon in an amount of 5% by weight based on the total catalyst, and ethanol (100 g) as the solvent were charged in an autoclave made of SUS (internal volume: 1000 ml). After heating to 150° C., the inside of the autoclave was pressurized to 25 kg/cm$^2$G with hydrogen and the reduction reaction was conducted for 2.3 hours.

After the completion of the reduction reaction, the ruthenium catalyst was removed from the reduction reaction mixed solution by filtration. The resultant reduction reaction mixture was analyzed by gas chromatography. As a result, 41% of 3-(2-hydroxycyclohexyl)methyl propionate and 43% of octahydrocoumarin were contained in the reduction reaction mixture, but 3,4-dihydrocoumarin was not detected.

Example 5

3,4-dihydrocoumarin (100 g), a catalyst (5 g) composed of active carbon and ruthenium supported thereon in an amount of 5% by weight based on the total catalyst, and pentanol (100 g) as the solvent were charged in an autoclave made of SUS (internal volume: 1000 ml). After heating to 100° C., the inside of the autoclave was pressurized to 15.5 kg/cm²G with hydrogen and the reduction reaction was conducted for 2.5 hours.

After the completion of the reduction reaction, the ruthenium catalyst was removed from the reduction reaction mixed solution by filtration. The resultant reduction reaction mixture was analyzed by gas chromatography. As a result, 38% of 3-(2-hydroxycyclohexyl)methyl propionate and 49% of octahydrocoumarin were contained in the reduction reaction mixture, but 3,4-dihydrocoumarin was not detected.

Example 6

3,4-dihydrocoumarin (100 g), a catalyst (10 g) composed of alumina and ruthenium supported thereon in an amount of 5% by weight based on the total catalyst, and methanol (100 g) as the solvent were charged in an autoclave made of SUS (internal volume: 1000 ml). After heating to 150° C., the inside of the autoclave was pressurized to 25 kg/cm²G with hydrogen and the reduction reaction was conducted for 14 hours.

After the completion of the reduction reaction, the ruthenium catalyst was removed from the reduction reaction mixed solution by filtration. The resultant reduction reaction mixture was analyzed by gas chromatography. As a result, 28% of 3-(2-hydroxycyclohexyl)methyl propionate and 65% of octahydrocoumarin were contained in the reduction reaction mixture, but 3,4-dihydrocoumarin was not detected.

Example 7

Coumarin (100 g), a catalyst (1 g) composed of active carbon and ruthenium supported thereon in an amount of 5% by weight based on the total catalyst, and methanol (100 g) as the solvent were charged in an autoclave made of SUS (internal volume: 1000 ml). After heating to 130° C., the inside of the autoclave was pressurized to 19.5 kg/cm²G with hydrogen and the reduction reaction was conducted for 9 hours.

After the completion of the reduction reaction, the ruthenium catalyst was removed from the reduction reaction mixed solution by filtration to obtain 201 g of the reaction mixed solution. The resultant reduction reaction mixture was analyzed by gas chromatography. As a result, 59% of 3-(2-hydroxycyclohexyl)methyl propionate and 22% of octahydrocoumarin were contained in the reduction reaction mixture, but coumarin was not detected.

Example 8

Coumarin (22 g), 3,4-dihydrocoumarin (18 g), octahydrocoumarin (56 g), a catalyst (2.5 g) composed of active carbon and ruthenium supported thereon in an amount of 5% by weight based on the total catalyst, and methanol (50 g) as the solvent were charged in an autoclave made of SUS (internal volume: 1000 ml). After heating to 100° C., the inside of the autoclave was pressurized to 15.5 kg/cm²G with hydrogen and the reduction reaction was conducted for 10 hours.

After the completion of the reduction reaction, the ruthenium catalyst was removed from the reduction reaction mixed solution by filtration obtain 149 g of the reaction mixed solution. The resultant reduction reaction mixture was analyzed by gas chromatography. As a result, 55% of 3-(2-hydroxycyclohexyl)methyl propionate and 35% of octahydrocoumarin were contained in the reduction reaction mixture, but coumarin and 3,4-dihydrocoumarin were not detected.

Example 9

202 g of the reduction reaction mixture obtained by the same method described in Example 1 was cooled, and then the solvent was removed by conducting a simple distillation under a normal pressure. The simple distillation was continuously conducted by heating at a maximum temperature of 150° C. under a pressure of 8 mmhg, thereby conducting the intramolecular dealcoholization reaction. As a result, 68 g of an effluent was obtained. The resultant effluent was analyzed by gas chromatography. As a result, 96% by weight of octahydrocoumarin was contained in the resultant effluent, but 3-(2-hydroxycyclohexyl)methyl propionate was not detected. The yield of octahydrocoumarin was 65% based on the charged amount of 3,4-dihydrocoumarin.

Comparative Example 1

3,4-dihydrocoumarin (100 g) and a catalyst (5 g) composed of active carbon and ruthenium supported thereon in an amount of 5% by weight based on the total catalyst, in the absence of an alcohol, were charged in an autoclave made of SUS (internal volume: 1000 ml). After heating to 150° C., the autoclave was pressurized to 25 kg/cm²G with hydrogen and the reduction reaction was conducted for 2.5 hours.

After the completion of the reduction reaction, the ruthenium catalyst was removed from the reduction reaction mixed solution by filtration. The resultant reduction reaction mixture was analyzed by gas chromatography. As a result, 55% of cyclohexylpropionic acid and 33% of octahydrocoumarin were contained in the reduction reaction mixture, but 3,4-dihydrocoumarin was not detected.

Comparative Example 2

3,4-dihydrocoumarin (100 g), a catalyst (5 g) composed of active carbon and ruthenium supported thereon in an amount of 5% by weight based on the total catalyst, and cyclohexane (100 g) as the solvent, in the absence of an alcohol, were charged in an autoclave made of SUS (internal volume: 1000 ml). After heating to 150° C., the inside of the autoclave was pressurized to 25 kg/cm²G with hydrogen and the reduction reaction was conducted for 3.7 hours.

After the completion of the reduction reaction, the ruthenium catalyst was removed from the reduction reaction mixed solution by filtration. The resultant reduction reaction mixture was analyzed by gas chromatography. As a result, 55% of cyclohexylpropionic acid and 34% of octahydrocoumarin were contained in the reduction reaction mixture, but 3,4-dihydrocoumarin was not detected.

Comparative Example 3

3,4-dihydrocoumarin (100 g), a catalyst (5 g) composed of active carbon and ruthenium supported thereon in an amount of 5% by weight based on the total catalyst, and ethyl acetate (100 g) as the solvent, in the absence of an alcohol, were charged in an autoclave made of SUS (internal volume: 1000 ml). After heating to 150° C., the inside of the autoclave was pressurized to 25 kg/cm²G with hydrogen and the reduction reaction was conducted for 2.8 hours.

After the completion of the reduction reaction, the ruthenium catalyst was removed from the reduction reaction mixed solution by filtration. The resultant reduction reaction mixture was analyzed by gas chromatography. As a result, 52% of cyclohexylpropionic acid and 35% of octahydrocoumarin were contained in the reduction reaction mixture, but 3,4-dihydrocoumarin was not detected.

Comparative Example 4

3,4-dihydrocoumarin (100 g), a catalyst (5 g) composed of active carbon and platinum supported thereon in an amount of 5% by weight based on the total catalyst, and methanol (100 g) as the solvent, in the absence of a ruthenium catalyst, were charged in an autoclave made of SUS (internal volume: 1000 ml). After heating to 150° C., the inside of the autoclave was pressurized to 25 kg/cm²G with hydrogen and the reduction reaction was conducted for 6 hours.

After the completion of the reduction reaction, the platinum catalyst was removed from the reduction reaction mixed solution by filtration. The resultant reduction reaction mixture was analyzed by gas chromatography. As a result, 100% of 3,4-dihydrocoumarin and 3-(2-hydroxyphenyl) methyl propionate were contained in the reduction reaction mixture, but octahydrocoumarin was not detected.

Comparative Example 5

3,4-dihydrocoumarin (100 g), a catalyst (5 g) composed of active carbon and palladium supported thereon in an amount of 5% by weight based on the total catalyst, and methanol (100 g) as the solvent, in the absence of a ruthenium catalyst, were charged in an autoclave made of SUS (internal volume: 1000 ml). After heating to 150° C., the inside of the autoclave was pressurized to 25 kg/cm²G with hydrogen and the reduction reaction was conducted for 6 hours.

After the completion of the reduction reaction, the palladium catalyst was removed from the reduction reaction mixed solution by filtration. The resultant reduction reaction mixture was analyzed by gas chromatography. As a result, 100% of 3,4-dihydrocoumarin and 3-(2-hydroxyphenyl) methyl propionate were contained in the reduction reaction mixture, but octahydrocoumarin was not detected.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. A process for producing octahydrocoumarins represented by the general formula (1):

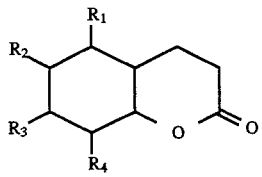

wherein $R_1$ to $R_4$ respectively indicate a hydrogen atom or an alkyl group having 1 to 5 carbon atoms, which comprises the step of reducing one or more coumarins represented by the general formula (2):

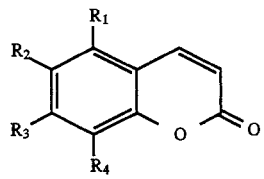

wherein $R_1$ to $R_4$ respectively indicate a hydrogen atom or an alkyl group having 1 to 5 carbon atoms, or reducing one or more 3,4-dihydrocoumarins represented by the general formula (3):

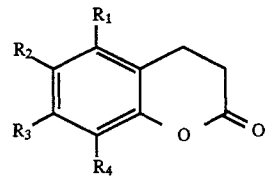

wherein $R_1$ to $R_4$ respectively indicate a hydrogen atom or an alkyl group having 1 to 5 carbon atoms, or reducing a mixture of one or more coumarins and one or more 3,4-dihydrocoumarins, with hydrogen in the presence of at least one alcohol and at least one ruthenium catalyst.

2. The process according to claim 1, wherein the at least one alcohol is an alcohol having 1 to 6 carbon atoms.

3. The process according to claim 1, further comprising a step of heating a reduction reaction mixture obtained from the reducing step.

4. The process according to claim 3, further comprising a step of removing the at least one alcohol from the reduction reaction mixture obtained.

5. The process according to claim 1, wherein the one or more coumarins is coumarin and the one or more 3,4-dihydrocoumarins is 3,4-dihydrocoumarin.

6. The process according to claim 1, wherein the coumarin is at least one member selected from the group consisting of coumarin, 5-methylcoumarin, 6-methylcoumarin, 7-methylcoumarin, 8-methylcoumarin, 5-ethylcoumarin, 6-ethylcoumarin, 7-ethylcoumarin, 8-ethylcoumarin, 5,6-dimethylcoumarin, 5,7-dimethylcoumarin, 5,8-dimethylcoumarin, 6,7-dimethylcoumarin, 6,8-dimethylcoumarin, 7,8-dimethylcoumarin, 5-methyl-6-ethyl-coumarin, 5-methyl-7-ethyl-coumarin, 5-methyl-8-ethyl-coumarin, 6-methyl-7-ethyl-coumarin, 6-methyl-8-ethyl-coumarin, 7-methyl-8-ethyl-coumarin, 5-ethyl-6-methyl-coumarin, 5-ethyl-7-methyl-coumarin, 5-ethyl-8-methyl-coumarin, 6-ethyl-7-methyl-coumarin, 6-ethyl-8-methyl-coumarin, and 7-ethyl-8-methyl-coumarin.

7. The process according to claim 1, wherein the 3,4-dihydrocoumarin is at least one member selected from the group consisting of 3,4-dihydrocoumarin, 5-methyl-3,4-dihydrocoumarin, 6-methyl-3,4-dihydrocoumarin, 7-methyl-3,4-dihydrocoumarin, 8-methyl-3,4-dihydrocoumarin, 5-ethyl-3,4-dihydrocoumarin, 6-ethyl-3,4-dihydrocoumarin, 7-ethyl-3,4-dihydrocoumarin, 8-ethyl-3,4-dihydrocoumarin, 5,6-dimethyl-3,4-dihydrocoumarin, 5,7-dimethyl-3,4-dihydrocoumarin, 5,8-dimethyl-3,4-dihydrocoumarin, 6,7-dimethyl-3,4-dihydrocoumarin, 6,8-dimethyl-3,4-dihydrocoumarin, 7,8-dimethyl-3,4-dihydrocoumarin, 5-methyl-6-ethyl-3,4-dihydrocoumarin, 5-methyl-7-ethyl,3,4-dihydrocoumarin, 5-methyl-8-ethyl-3,4-dihydrocoumarin, 6-methyl-7-ethyl-3,4-dihydrocoumarin, 6-methyl-8-ethyl-3,4-dihydrocoumarin, 7-methyl-8-ethyl-3,4-dihydrocoumarin, 5-ethyl-6-methyl-3,4-dihydrocoumarin, 5-ethyl-7-methyl-3,4-dihydrocoumarin, 5-ethyl-8-methyl-3,4-dihydrocoumarin, 6-ethyl-7-methyl-3,4-dihydrocoumarin, 6-ethyl-8-methyl-3,4-dihydrocoumarin, and 7-ethyl-8-methyl-3,4-dihydrocoumarin.

8. The process according to claim 1, wherein the alcohol is at least one member selected from the group consisting of methanol, ethanol, propanol, isopropanol, pentanol, cyclopentanol, hexanol, cyclohexanol, and amyl alcohol.

9. The process according to claim 1, wherein the at least one alcohol is present in an amount from about 0.5 to about 100 mol, based on 1 mol of the one or more coumarins, or the one or more 3,4-dihydrocoumarins, or the mixture of one or more coumarins and one or more 3,4-dihydrocoumarins.

10. The process according to claim 1, wherein the at least one ruthenium catalyst comprises ruthenium having a valence of 0 to 6, and is selected from the group of catalysts consisting of metal ruthenium, ruthenium chloride, ruthenium oxide, and organic ruthenium compounds.

11. The process according to claim 1, wherein the at least one ruthenium catalyst comprises ruthenium supported on a carrier selected from the group consisting of group 2, 13, 14, or 16 elements of the periodic table, or compounds thereof.

12. The process according to claim 11, wherein the ruthenium supported on the carrier is in an amount from about 0.1 to about 20% by weight, based on the total amount of the at least one ruthenium catalyst.

13. The process according to claim 1, wherein ruthenium is contained in the at least one ruthenium catalyst in an amount from about 0.0001 to about 1% by weight, based on the total amount of the one or more coumarins, or the one or more 3,4-dihydrocoumarins, or the mixture of one or more coumarins and one or more 3,4-dihydrocoumarins.

14. The process according to claim 1, wherein the one or more coumarins, or the one or more 3,4-dihydrocoumarins, or the mixture of one or more coumarins and one or more 3,4-dihydrocoumarins are reduced at a reaction temperature from about 50° C. to about 250° C. and at a hydrogen partial pressure from about 0.5 to about 100 atm.

15. The process according to claim 3, wherein the step of heating the reduction reaction mixture is conducted at a temperature from about 50° C. to about 300° C., and in the presence of an acid catalyst selected from the group consisting of mineral acids, carboxylic acids and solid acids, or in the presence of a base catalyst selected from the group consisting of sodium hydroxide, potassium hydroxide, sodium carbonate, amines and basic ion exchange resin.

* * * * *